United States Patent [19]

Takazawa et al.

[11] Patent Number: 5,219,752
[45] Date of Patent: Jun. 15, 1993

[54] PROCESS FOR CONTINUOUSLY CULTURING ADHERENT ANIMAL CELLS

[75] Inventors: Yoshiharu Takazawa, Hino; Michiyuki Tokashiki, Hachioji, both of Japan

[73] Assignee: Teijin, Limited, Osaka, Japan

[21] Appl. No.: 730,386

[22] Filed: Jul. 15, 1991

Related U.S. Application Data

[63] Continuation of Ser. No. 356,366, May 24, 1989, abandoned.

[30] Foreign Application Priority Data

May 25, 1988 [JP] Japan ................. 63-125664
Aug. 19, 1988 [JP] Japan ................. 63-204733

[51] Int. Cl.$^5$ .................. C12N 5/08; C12P 21/00
[52] U.S. Cl. ................. 435/240.25; 435/70.3
[58] Field of Search ............... 435/240.24, 240.25, 435/240.31, 70.3

[56] References Cited

U.S. PATENT DOCUMENTS 4,059,485 11/1977 Tolbert et al. ............... 435/240.25
4,184,916 1/1980 Tolbert et al. ............... 435/240.25
4,560,655 12/1985 Baker ....................... 435/240.25
5,114,855 5/1992 Hu et al. ................... 435/240.24

OTHER PUBLICATIONS

Eagle, Amino Acid Metabolism in Mammalian Cell Culture Science, vol. 130, pp. 432–437 1959.
Nagafuchi, et al., Transformation of Cell Adhesion Properties by Exogenously Introduced E-Cadherin cDNA, Nature, vol. 329, pp. 341–343 24 Sep. 1987.

*Primary Examiner*—David L. Lacey
*Assistant Examiner*—George C. Elliott
*Attorney, Agent, or Firm*—Wenderoth, Lind & Ponack

[57] ABSTRACT

Adherent 293 human kidney cells are continuously cultured in suspension in serum-free medium. Fresh medium is fed into a culture vessel and spent medium is withdrawn from the vessel. The 293 cells are maintained in small aggregates in suspension at a density of at least $3 \times 10^6$ cells/ml for 30 days. The formation of large cell clumps is prevented by maintaining the concentration of calcium in the serum-free medium at 0.002 mM to 0.3 mM.

7 Claims, 1 Drawing Sheet

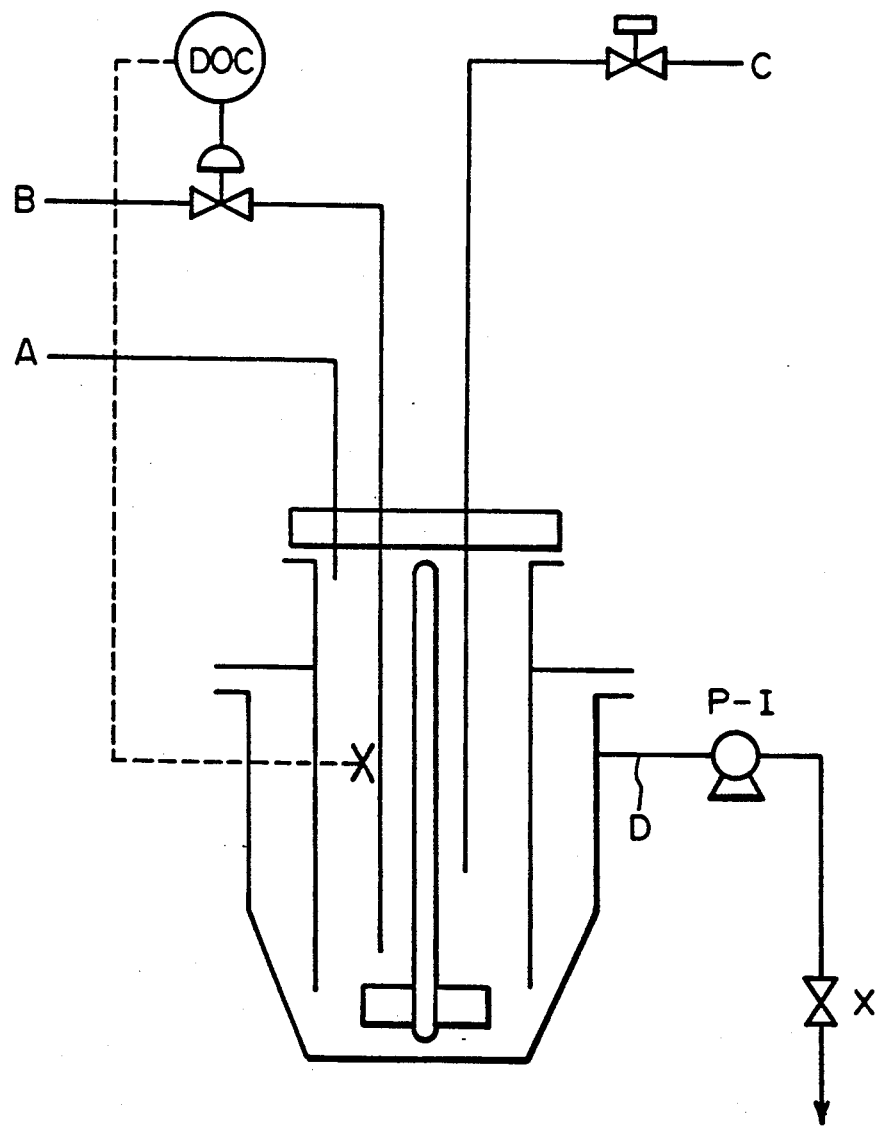

— 1 —

PROCESS FOR CONTINUOUSLY CULTURING ADHERENT ANIMAL CELLS

This application is a continuation of now abandoned application. Ser. No. 07/356,366, filed May 24, 1989.

BACKGROUND OF THE INVENTION a. Field of the Invention

This invention relates to a process for continuously culturing adherent animal cells, and more specifically, to a process for continuously culturing adherent animal cells in suspension.

b. Description of the Prior Art

Culturing of cells in large quantities on an industrial scale is a technique which is important in the production of various hormones, enzymes, lymphokines, nucleic acids, antibiotics and other useful biologically active substances. In many cases, cells producing these biologically active useful substances, particularly transformed cells having inserted DNA so as to permit secretion of the desired substances are adherent, and it is an industrially important problem to develop a technique of efficiently culturing these cells.

Some methods of culturing large amounts of adherent cells and devices therefor have previously been proposed. Many of them, however, are directed to the growth of the cells adhering to the surface of a solid carrier, and give rise to problems in regard to scale-up, operability and stability in long-term continuous operation. For example, the microcarrier culturing method developed by Van Wezel is excellent and involves culturing cells on microcarriers whereby they can be cultured in suspension in a tank [see Growth of Cell Strains and Primary Cells on Microcarriers in Homogeneous Culture, Nature 216, 64–65 (1967)]. However, according to the culturing method of Van Wezel et al., the culture area depends upon the area of the microcarrier, and when the culturing is continued for a long period of time, the cells are gradually come off from the microcarriers.

U.S. Pat. No. 4,059,485 describes an attempt to culture adherent cells in suspension in a serum-containing medium. This method, however, has the disadvantage that as the culture is continued, the adherent cells aggregate to form large masses, and the cells in the large masses necrotize.

To the best of the knowledge of the present inventors, there has been no industrial technique of culturing adherent animal cells in suspension by themselves continuously over long periods of time without forming large aggregated cell clumps.

c. Objects of the Invention

It is an object of this invention to provide a process by which adherent animal cells can be cultured in suspension without using solid carriers such as microcarriers.

Another object of this invention is to provide an industrial process by which adherent animal cells can be cultured in suspension continuously over long periods of time.

Still another object of this invention is to provide an industrial process by which adherent animal cells can be cultured continuously over long periods of time while maintaining the cells themselves or relatively small aggregated particles in suspension.

Yet another object of this invention is to provide a process by which adherent animal cells can be cultured in suspension in a very high density.

A further object of this invention is to provide a process by which adherent animal cells can be cultured in suspension by using a serum-free culture medium.

A still further object of this invention is to provide a process by which adherent animal cells which secrete a useful biologically active substance are cultured in suspension, the culture broth is taken out from the culture tank, and the useful biologically active substance is recovered continuously and stably from the culture broth.

Additional objects of the invention will become apparent from the following description.

DETAILED DESCRIPTION OF THE INVENTION

In order to achieve the above objects of the invention, the present inventors have undertaken investigations on a process by which adherent animal cells can be cultured in suspension without using solid carriers such as microcarriers. These investigations led to the finding that the concentration of a calcium ion in the medium is closely related with the aggregation of the cells into masses. In serum-containing media or certain serum-free media generally used in the culturing of animal cells, a calcium ion exists in the form of calcium chloride, calcium pantothenate or another calcium salt, usually in a concentration of 0.3 mM, in many cases more than 0.5 mM.

When adherent animal cells are cultured in suspension in a medium with an ordinary calcium concentration, the cells gradually adhere to one another and clump or aggregate and finally become large masses.

When the number of cells per mass is at least 100, particularly more than 300, oxygen and nutrients do not sufficiently reach cells existing in the interior of the masses, and they lose the proliferating ability and the ability to secrete the useful biologically active substance, and in many cases die away.

It has been found unexpectedly that if the calcium ion concentration in the medium under the culturing conditions is decreased, particularly to less than 0.3 mM, preferably less than 0.25 mM, the adherent animal cells even in a high density do not become large masses and can be cultured for long periods of time in suspension by themselves or as relatively small particles.

It has also been found that if the calcium ion concentration in the medium is decreased below 0.02 mM, particularly below 0.002 mM, the growth or proliferation of the cells becomes difficult, or their ability to secrete the useful biologically active substance is abruptly decreased, but that by maintaining the calcium ion concentration within a specific range, the adherent animal cells can be grown in suspension for long periods of time, and their ability to secrete the useful biologically active substances is not adversely affected.

According to the present invention, there is provided a process for continuously culturing adherent animal cells in a serum-free medium, characterized in that (1) a fresh medium is fed into a culture vessel, and a spent medium is withdrawn from the vessel, (2) the adherent animal cells in the serum-free medium in the vessel are maintained in suspension, (3) the adherent animal cells in suspension are caused to exist at a density of at least $3 \times 10^6$ cells/ml, and (4) the concentration of a calcium ion in the medium under the culturing conditions is maintained at 0.002 mM to 0.3 mM.

Some pieces of information are available from the prior literature on the effect of a calcium ion upon the cultivation of animal cells. For example, the following references may be cited, and will be discussed at some length.

(a) Science, vol. 130, 432–437 (1959)

This is a paper entitled "Amino Acid Metabolism in Mammalian Cell Cultures". Table 1 at page 433 shows a minimum essential medium for cultivation of mammalian cells in either monolayer or suspension. It is described that the concentration of the calcium ion ($Ca^{++}$) in this essential medium is 1.8 mM or 0 (see the row for $CaCl_2$ in the column of component).

As an explanation of Table 1, it is stated: "In using this medium for the growth of cells in suspension, $Ca^{++}$ should be omitted or greatly reduced in order to minimize clumping (see 43). W. F. McLimens, J. Immunol. 79, 428 (1957) as the citation 43 states at page 42, left column, lines 6-9: "Strain HeLa (Gey) was cultured in medium consisting of human, calf or horse serum, 10%; Eagle's mixture (9) in Earle's balanced salt solution, 90% ....". From this statement, it is presumed that the medium used in the above culture has a calcium ion concentration of at least 1.85 mM. Specifically, 10% serum contains about 0.25 mM of a calcium ion, and since the Earle's balanced salt solution is known to contain 200 mg/liter of $CaCl_2$, 90% of this salt solution contains about 1.6 mM of a calcium ion. As a result, the mixed medium containing 10% serum and 90% salt solution contains about 1.85 mM of a calcium ion.

Accordingly, although the reference states that $Ca^{++}$ should be omitted, it is apparent from the foregoing that at the medium actually used contains $Ca^{++}$ in a relatively high concentration of about 1.85 mM. Thus, although the reference discloses that at this $Ca^{++}$ concentration level clumping of cells was minimized, it cannot immediately be expected from this disclosure that cells in small aggregated masses as in the present invention are grown at a high density for a long period of time. The above reference does not at all suggests that adherent cells are cultured in suspension at a high density by using a serum-free medium.

(b) Journal of Experimental Medicine, Vol. 152, 469–474 (1980)

This reference states as page 46: "HeLa-S3 cells were grown in suspension in the spinner modification of Eagle's minimum essential medium (spinner medium) supplemented with 4% fetal calf serum. The initial cell concentration was $2 \times 10^4$ cells/ml." This statement, however, merely shows the results obtained by examining the effect of the concentration of interferon in this culture upon all surface receptors for the lectin concanavalin A. It does not at all describe the state of high density cells, particularly their clumping at low calcium ion concentration.

(c) Nature, Vol. 329, 341 (24 September 1987)

This paper describes "Transformation of cell adhesion properties by exogenously introduced E-cadherin cDNA". Table 1 at page 343 shows the results obtained by examining the $Ca^{++}$-dependent aggregation of untransformed and transformed L and F9 cells. Table 1 shows the degrees of aggregation in the presence of 1 mM $Ca^{++}$ and in the absence of $Ca^{++}$ Table 1 indicates that according to the type of the cells, the degree of aggregation may or may not depend upon the presence of $Ca^{++}$, and generally in the absence of $Ca^{30+}$,aggregation does not occur. In the experiment shown in Table 1, however, the state of cell aggregation was examined only 30 minutes after the incubation, and no state of aggregation was examined after long-term cultivation. Furthermore, this paper is quite silent on the type of the medium used and the cell density. When $Ca^{++}$, the cells themselves cannot survive. This reference therefore fails to suggest the present invention.

(d) IN VITRO, 16(6), 486–490 (1980)

This reference describes "cell aggregate suspension culture for large-scale production of biomolecules". It shows that when SV3T3 cells were cultured in Dulbecco's modified Eagle's medium containing 10% fetal bovine serum (presumably this medium contains about 2 mM of $Ca^{++}$, and very large cell blocks were formed.

This reference, however, does not at all describe that when the culture is carried out at a high cell density in a serum-free medium as in the present invention, the aggregation of cells is adjusted by maintaining the $Ca^{++}$ concentration at a relatively low level.

The invention will now be described in greater detail.

The cells to be cultured in accordance with this invention are adherent animal cells. The adherent cells denote cells of the type which after cultivation in a serum-containing medium in a tissue culture dish, cannot be separated as living single cells by pipetting.

Suitable adherent animal cells for use in the process of this invention have the property of forming clumps containing at least 100 cells per clump on an average when they are cultured in suspension with stirring in an ordinary medium for animal cells for about 5 days. The ordinary medium contains a calcium ion in a concentration of 0.3 to 1.8 mM.

The adherent animal cells used in the process of this invention, so long as they have the aggregating property, may be not only natural normal cells, but also non-artificially or artificially (e.g., by gene manipulation) modified cells. The present invention is particularly suitable for culturing cells which secrete a useful biologically active substance. Since in the process of this invention, cells can be cultured at a high density and the culture broth is taken out, the useful biologically active substance secreted by the cells can be separated in a high concentration from the culture broth.

Thus, according to the process of this invention, adherent animal cells secreting a useful biologically active substance can be cultured in suspension as single cells or small cell clumps in a serum-free medium, and the culturing can be carried out at a high cell density continuously for a long period of time. Hence, according to the invention, the culture broth taken out from the culture system contains the useful biologically active substance in a high concentration and its separation is economically advantageous. Accordingly, the useful biologically active substance can be industrially produced continuously and stably.

Specific examples of the adherent animal cells that can be cultured in accordance with this invention are tabulated below. It should be understood however that the present invention is not limited to these specific examples and modified cells thereof can also be used as the adherent animal cells in this invention. The following table indicates species/tissue and ATCC numbers together with cell names.

| Species/Tissue | Name | ATCC No. | Page No. |
|---|---|---|---|
| Bat | | | |
| lung | Tbl Lu | CCL 88 | 50 |
| | | | 247 |
| Bluegill | | | |
| trunk | BF2 | CCL 91 | 52 |
| Bovine | | | |
| endothelium | CPA | CCL 207 | 106 |
| | CPAE | CCL 209 | 107 |
| heart | FBHE | CRL 1395 | 130 |
| kidney | MDBK | CCL 22 | 15 |
| trachea | EBTr | CCL 44 | 25 |
| turbinate | BT | CRL 1390 | 130 |
| Buffalo | | | |
| lung | Bu | CCL 40 | 23 |
| Bullfrog | | | |
| tongue | FT | CCL 41 | 23 |
| Bullhead | | | |
| trunk | BB | CCL 59 | 33 |
| Cat | | | |
| kidney | CRFK | CCL 94 | 54 |
| lung | AK-D | CCL 150 | 83 |
| | Fe2Lu | CCL 217 | 111 |
| tongue | Fc3Tg | CCL 176 | 95 |
| Chiken | | | |
| embryo | SL-29 | CRL 1590 | 139 |
| Chimpanzee | | | |
| skin | WES | CRL 1609 | 141 |
| Dog | | | |
| bone | D-17 | CCL 183 | 95 |
| kidney | DoCl$_1$ | CCL 34.1 | 20 |
| | MDCK | CCL 34 | 19 |
| thymus | Cf2Th | CRL 1430 | 131 |
| (unknown) | A-72 | CRL 1542 | 135 |
| Dolphin | | | |
| kidney | Sp 1 K | CCL 78 | 44 |
| Duck | | | |
| embryo | | CCL 141 | 78 |
| Ferret | | | |
| brain | Mpf | CRL 1656 | 146 |
| Fox | | | |
| lung | Folu | CCL 168 | 93 |
| Frog | | | |
| embryo | ICR 2A | CCL 145 | 80 |
| | ICR 134 | CCL 128 | 71 |
| tongue | FT | CCL 41 | 23 |
| Gekko | | | |
| lung | GL1 | CCL 111 | 62 |
| Gerbil | | | |
| fibroma | IMR-33 | CCL 146 | 80 |
| lung | GeLu | CCL 100 | 57 |
| Gibbon | | | |
| lymphosarcoma | MLA 144 | TIB 201 | 244 |
| Goat | | | |
| esophagus | Ch 1 Es | CCL 73 | 40 |
| Goldfish | | | |
| fin | CAR | CCL 71 | 39 |
| Goose | | | |
| sternum | CGBQ | CCL 169 | 94 |
| Grunt | | | |
| fin | GF | CCL 58 | 32 |
| Guinea pig | | | |
| colon adenocarcinoma | GPC-16 | CCL 242 | 124 |
| fetus, transformed | 104Cl | CRL 1405 | 130 |
| lung | JH4 Clone 1 | CCL 158 | 86 |
| Hamster | | | |
| kidney | BHK-21 | CCL 10 | 9 |
| | Hak | CCL 15 | 12 |
| | tk-ts13 | CRL 1632 | 143 |
| lung | AHL-1 | CCL 195 | 101 |
| | Dede | CCL 39 | 22 |
| | Don | CCL 16 | 12 |
| melanoma | FF | CRL 1479 | 133 |
| | RPMI 1846 | CCL 49 | 28 |
| muscle | DDT$_1$MF2 | CRL 1701 | 150 |

-continued

| Species/Tissue | Name | ATCC No. | Page No. |
|---|---|---|---|
| ovary | CHO-K1 | CCL 61 | 34 |
| peritoneum | B14FAF28-G3 | CCL 14 | 11 |
| | NCTC 4206 | CCL 14.2 | 11 |
| somatic cells | R 1610 | CRL 1657 | 146 |
| Horse | | | |
| dermis | E. Derm | CCL 57 | 32 |
| Human | | | |
| adrenal cortex | SW-13 | CCL 105 | 59 |
| amnion | AV$_3$ | CCL 21 | 14 |
| | FL | CCL 62 | 34 |
| | WISH | CCL 25 | 16 |
| ascitic fluid | CA46 | CRL 1648 | 145 |
| | Jiyoye | CCL 87 | 50 |
| | P3HR-1 | HTB 62 | 184 |
| | ST486 | CRL 1647 | 145 |
| bladder | HS 738B1 | HTB 160 | 208 |
| | HT-1197 | CRL 1473 | 133 |
| | HT-1376 | CRL 1472 | 133 |
| | J82 | HTB 1 | 165 |
| | RT4 | HTB 2 | 165 |
| | SCaBER | HTB 3 | 165 |
| | TCCSUP | HTB 5 | 166 |
| | T24 | HTB 4 | 165 |
| | 5637 | HTB 9 | 166 |
| bone | RD-ES | HTB 166 | 209 |
| bone marrow | IM-9 | CCL 159 | 87 |
| | KG-1 | CCL 246 | 127 |
| | KG-1a | CCL 246.1 | 127 |
| brain | A-172 | CRL 1620 | 142 |
| | HS 683 | HTB 138 | 203 |
| | H 4 | HTB 148 | 206 |
| | TE 671 | HTB 139 | 203 |
| | T98G | CRL 1690 | 149 |
| | U-87MG | HTB 14 | 167 |
| | U-138MG | HTB 16 | 168 |
| | U-373MG | HTB 17 | 168 |
| breast | BT | HTB 19 | 169 |
| | BT-474 | HTB 20 | 170 |
| | BT-483 | HTB 121 | 197 |
| | BT-549 | HTB 122 | 198 |
| | Du4475 | HTB 123 | 198 |
| | HBL-100 | HTB 124 | 198 |
| | HS 578Bst | HTB 125 | 199 |
| | HS 578T | HTB 126 | 199 |
| | MCF7 | HTB 22 | 170 |
| | MDA-MB-134-VI | HTB 23 | 171 |
| | MDA-MB-157 | HTB 24 | 171 |
| | MDA-MB-175-VII | HTB 25 | 171 |
| | MDA-MB-231 | HTB 26 | 172 |
| | MDA-MB-330 | HTB 127 | 200 |
| | MDA-MB-361 | HTB 27 | 172 |
| | MDA-MB-415 | HTB 128 | 200 |
| | MDA-MB-435S | HTB 129 | 200 |
| | MDA-MB-436 | HTB 130 | 201 |
| | MDA-MB-453 | HTB 131 | 201 |
| | MDA-MB-468 | HTB 132 | 201 |
| | SK-BR-1 III | HTB 28 | 172 |
| | SK-BR-2 III | HTB 29 | 173 |
| | SK-BR-3 | HTB 30 | 173 |
| | T-47D | HTB 133 | 202 |
| | ZR-75-1 | CRL 1500 | 134 |
| | ZR-75-30 | CRL 1504 | 135 |
| bronchiole | CCD-14Br | CCL 203 | 104 |
| cervix | CaSki | CRL 1550 | 136 |
| | C-4 I | CRL 1594 | 139 |
| | C-4 II | CRL 1595 | 140 |
| | C-33A | HTB 31 | 174 |
| | HeLa | CCL 2 | 3 |
| | HeLa S3 | CCL 2.2 | 4 |
| | HeLa 229 | CCL 2.1 | 4 |
| | Hs602 | HTB 142 | 204 |
| | HT-3 | HTB 32 | 174 |
| | ME-180 | HTB 33 | 174 |
| | MS 751 | HTB 34 | 175 |
| | SiHa | HTB 35 | 175 |
| colon | Caco-2 | HTB 37 | 176 |
| | CCD-18Co | CRL 1459 | 133 |
| | CCD-33Co | CRL 1539 | 135 |
| | CCD-112CoN | CRL 1541 | 135 |

-continued

| Species/Tissue | Name | ATCC No. | Page No. |
|---|---|---|---|
| | COLO 201 | CCL 224 | 115 |
| | COLO 205 | CCL 222 | 114 |
| | COLO 320DM | CCL 220 | 112 |
| | COLO 320HSR | CCL 220.1 | 113 |
| | DLD-1 | CCL 221 | 114 |
| | HCMC | CCL 239 | 123 |
| | HCT-15 | CCL 225 | 116 |
| | HCT 116 | CCL 247 | 128 |
| | HT-29 | HTB 38 | 176 |
| | LoVo | CCL 229 | 118 |
| | LS 174T | CL 188 | 98 |
| | LS 180 | CL 187 | 97 |
| | SK-CO-1 | HTB 39 | 177 |
| | SW48 | CCL 231 | 119 |
| | SW403 | CCL 230 | 119 |
| | SW480 | CCL 228 | 117 |
| | SW620 | CCL 227 | 117 |
| | SW948 | CCL 237 | 121 |
| | SW1116 | CCL 233 | 120 |
| | SW1417 | CCL 238 | 122 |
| | WiDr | CCL 218 | 111 |
| conjunctiva | clone 1-5c-4 | CCL 20.2 | 13 |
| connective tissue | Hs 729 | HTB 153 | 207 |
| desmoid tumor | D422T | CRL 1659 | 146 |
| duodenum | HuTu 80 | HTB 40 | 177 |
| embryo | Hs173We | HTB 158 | 208 |
| endometrium | AN3CA | HTB 111 | 195 |
| | HEC-1-A | HTB 112 | 195 |
| | HEC-1-B | HTB 113 | 196 |
| | KLE | CRL 1622 | 143 |
| | RL95-2 | CRL 1671 | 147 |
| eye | Y79 | HTB 18 | 169 |
| fibrosarcoma | Hs913T | HTB 152 | 207 |
| | HT-1080 | CCL 121 | 67 |
| intestine, small | FHs 74 Int | CCL 241 | 124 |
| | HCT-8 | CCL 244 | 115 |
| | HISM | CRL 1692 | 149 |
| | Intestine 407 | CCL 6 | 5 |
| kidney | A-498 | HTB 44 | 178 |
| | A-704 | HTB 45 | 179 |
| | ACHN | CRL 1611 | 142 |
| | Caki-1 | HTB 46 | 179 |
| | Caki-2 | HTB 47 | 179 |
| | G-401 | CRL 1441 | 132 |
| | G-402 | CRL 1440 | 132 |
| | SK-NEP-1 | HTB 48 | 180 |
| | 293 | CRL 1573 | 137 |
| larynx | HEp-2 | CCL 23 | 15 |
| liver | Chang liver | CCL 13 | 10 |
| | CLCL | CL 99 | 57 |
| | SK-HEP-1 | HTB 52 | 180 |
| | WRL 68 | CL 48 | 28 |
| | Hep 3B | HB8064 | |
| | Hep G2 | HB8065 | |
| lung | A 427 | HTB 53 | 181 |
| | A 549 | CCL 185 | 96 |
| | Calu-1 | HTB 54 | 181 |
| | Calu-3 | HTB 55 | 182 |
| | Calu-6 | HTB 56 | 182 |
| | CCD-8 Lu | CCL 201 | 104 |
| | CCD-11 Lu | CCL 202 | 104 |
| | CCD-13 Lu | CCL 200 | 103 |
| | CCD-14 Br | CCL 203 | 104 |
| | CCD-16 Lu | CCL 204 | 105 |
| | CCD-18 Lu | CCL 205 | 105 |
| | CCD-19 Lu | CCL 210 | 108 |
| | CCD-25 Lu | CCL 215 | 110 |
| | CCD-29 Lu | CRL 1478 | 133 |
| | CCD-32 Lu | CRL 1485 | 134 |
| | CCD-33 Lu | CRL 1490 | 134 |
| | CCD-34 Lu | CRL 1491 | 134 |
| | CCD-37 Lu | CRL 1496 | 134 |
| | CCD-39 Lu | CRL 1498 | 134 |
| | HEL 299 | CCL 137 | 76 |
| | HFL 1 | CCL 153 | 84 |
| | HLF-a | CCL 199 | 103 |
| | Hs 738 Lu | HTB 157 | 207 |
| | HS 888 Lu | CCL 211 | 108 |
| | IMR-90 | CCL 186 | 97 |
| | LL24 | CCL 151 | 83 |
| | LL29 | CCL 134 | 74 |
| | LL47 | CCL 135 | 75 |
| | LL86 | CCL 190 | 98 |
| | LL97A | CCL 191 | 99 |
| | L-132 | CCL 5 | 5 |
| | MRC-5 | CCL 171 | 94 |
| | MRC-9 | CCL 212 | 109 |
| | NCI-H69 | HTB 119 | 197 |
| | NCI-H128 | HTB 120 | 197 |
| | SK-LU-1 | HTB 57 | 183 |
| | SK-MES-1 | HTB 58 | 183 |
| | WI-26 | CCL 95 | 54 |
| | WI-26 VA4 | CCL 95.1 | 55 |
| | WI-38 | CCL 75 | 41 |
| | WI-38 VA13 subline2 RA | CCL 75.1 | 42 |
| | WI-1003 | CCL 154 | 84 |
| maxilla | EB1 | HTB 60 | 184 |
| | Raji | CCL 86 | 49 |
| melanoma | A-375 | CRL 1619 | 142 |
| | C32 | CRL 1585 | 138 |
| | C32TG | CRL 1579 | 138 |
| | G-361 | CRL 1424 | 131 |
| | HS294T | HTB 140 | 204 |
| | HS 695T | HTB 137 | 203 |
| | HT-144 | HTB 63 | 185 |
| | Malme-3M | HTB 64 | 185 |
| | RPMI-7951 | HTB 66 | 185 |
| | SK-MEL-1 | HTB 67 | 186 |
| | SK-MEL-2 | HTB 68 | 186 |
| | SK-MEL-3 | HTB 69 | 186 |
| | SK-MEL-5 | HTB 70 | 187 |
| | SK-MEL-24 | HTB 71 | 187 |
| | SK-MEL-28 | HTB 72 | 188 |
| | SK-MEL-31 | HTB 73 | 188 |
| | WM-115 | CRL 1675 | 148 |
| | WM-266-4 | CRL 1676 | 148 |
| mouth | KB | CCL 17 | 13 |
| nasal septum | RPMI 2650 | CCL 30 | 17 |
| neuroblastoma | IMR-32 | CCL 127 | 70 |
| | SK-N-MC | HTB 10 | 167 |
| | SK-N-SH | HTB 11 | 167 |
| ovary | Caov-3 | HTB 75 | 188 |
| | Caov-4 | HTB 76 | 189 |
| | EB2 | HTB 61 | 184 |
| | NIH:OVCAR-3 | HTB 161 | 208 |
| | PA-1 | CRL 1572 | 137 |
| | SK-OV-3 | HTB 77 | 189 |
| palate | HEPM | CRL 1486 | 134 |
| pancreas | ASPC-1 | CRL 1682 | 148 |
| | BxPC-3 | CRL 1687 | 148 |
| | Capan-1 | HTB 79 | 189 |
| | Capan-2 | HTB 80 | 190 |
| | HS 766T | HTB 134 | 202 |
| | MIA PaCa-2 | CRL 1420 | 131 |
| | PANC-1 | CRL 1469 | 133 |
| pharynx | Detroit 562 | CCL 138 | 76 |
| | FaDu | HTB 43 | 178 |
| placenta | BeWo | CCL 98 | 56 |
| | JAR | HTB 144 | 205 |
| | JEG-3 | HTB 36 | 176 |
| | 3A | CRL 1583 | 138 |
| | 3A-subE | CRL 1584 | 138 |
| prostate | DU 145 | HTB 81 | 190 |
| | PC-3 | CRL 1435 | 131 |
| rectum | SW837 | CCL 235 | 121 |
| | SW1463 | CCL 234 | 120 |
| sarcoma | A-204 | HTB 82 | 190 |
| | A673 | CRL 1598 | 140 |
| | Esa-1 | HTB 83 | 191 |
| | G-292, clone A141B1 | CRL 1423 | 131 |
| | HOS | CRL 1543 | 135 |
| | KHOS/NP | CRL 1544 | 135 |
| | KHOS/240S | CRL 1545 | 136 |
| | KHOS-321H | CRL 1546 | 136 |
| | MG-63 | CRL 1427 | 131 |
| | MNNG/HOS | CRL 1547 | 136 |
| | RD | CCL 136 | 75 |
| | Saos-2 | HTB 85 | 191 |

-continued

| Species/Tissue | Name | ATCC No. | Page No. |
|---|---|---|---|
| | SK-ES-1 | HTB 86 | 192 |
| | SK-ES-2 | HTB 87 | 192 |
| | SK-LMS-1 | HTB 88 | 192 |
| | SK-UT-1 | HTB 114 | 196 |
| | SK-UT-1B | HTB 115 | 196 |
| | U-2-OS | HTB 96 | 192 |
| skin | Amdur II | CCL 124 | 69 |
| | A-431 | CRL 1555 | 136 |
| | BUD-8 | CRL 1554 | 136 |
| | CHP 3 | CCL 132 | 73 |
| | CHP 4 | CCL 133 | 74 |
| | Citrullinemia | CCL 76 | 42 |
| | Cri du Chat | CCL 90 | 52 |
| | C 211 | CCL 123 | 68 |
| | Dempsey | CCL 28 | 17 |
| | Detroit 510 | CCL 72 | 39 |
| | Detroit 525 | CCL 65 | 37 |
| | Detroit 529 | CCL 66 | 37 |
| | Detroit 532 | CCL 54 | 30 |
| | Detroit 539 | CCL 84 | 48 |
| | Detroit 548 | CCL 116 | 64 |
| | Detroit 551 | CCL 110 | 61 |
| | Detroit 573 | CCL 117 | 64 |
| | GS-109-IV-8 | CRL 1672 | 148 |
| | GS-109-V-20 | CRL 1610 | 142 |
| | GS-109-V-21 | CRL 1643 | 144 |
| | GS-109-V-34 | CRL 1613 | 142 |
| | GS-109-V-63 | CRL 1614 | 142 |
| | HG 261 | CCL 122 | 67 |
| | HS 27 | CRL 1634 | 144 |
| | HS 68 | CRL 1635 | 144 |
| | KD | CRL 1295 | 130 |
| | Malme-3 | HTB 102 | 193 |
| | WS 1 | CRL 1502 | 134 |
| stomach | HS 746T | HTB 135 | 202 |
| | KATO III | HTB 103 | 193 |
| submaxillary gland | A-253 | HTB 41 | 178 |
| testis | Cates-1B | HTB 104 | 194 |
| | Tera-1 | HTB 105 | 194 |
| | Tera-2 | HTB 106 | 194 |
| thymus | Hs 67 | HTB 163 | 208 |
| tongue | Scc-4 | CRL 1624 | 143 |
| | SCC-9 | CRL 1629 | 143 |
| | SCC-15 | CRL 1623 | 143 |
| | SCC-25 | CRL 1628 | 143 |
| uterus | AN3 CA | HTB 111 | 195 |
| | HEC-1-A | HTB 112 | 195 |
| | HEC-1-B | HTB 113 | 196 |
| | SK-UT-1 | HTB 114 | 196 |
| | SK-UT-1B | HTB 115 | 196 |
| vulva | SK-LMS-1 | HTB 88 | 192 |
| Iguana | | | |
| heart | 1gH-2 | CCL 108 | 61 |
| Marmoset | | | |
| leukocytes | B95-8 | CRL 1612 | 142 |
| Minipig | | | |
| kidney | MPK | CCL 166 | 92 |
| Mink | | | |
| lung | MiCl₁ | CCL 64.1 | 36 |
| | MV 1 Lu | CCL 64 | 35 |
| Minnow | | | |
| skin | FHM | CCL 42 | 24 |
| Monkey | | | |
| kidney | BS-C-1 | CCL 26 | 16 |
| | COS-1 | CRL 1650 | 145 |
| | COS-7 | CRL 1651 | 146 |
| | CV-1 | CCL 70 | 38 |
| | FRhK-4 | CRL 1688 | 149 |
| | LLC-MK₂ | CCL 7 | 6 |
| | LLC-MK₂ derivative | CCL 7.1 | 6 |
| | NCTC clone 3526 | CCL 7.2 | 7 |
| | OMK | CRL 1556 | 136 |
| | Vero | CCL 81 | 45 |
| | Vero C1008 | CRL 1586 | 138 |
| | Vero 76 | CRL 1587 | 139 |
| lung | DBS-FCL-1 | CCL 161 | 88 |
| | DBS-FCl-2 | CCL 162 | 88 |
| | DBS-FRhL-2 | CCL 160 | 87 |
| | DPSO 114/74 | CCL 194 | 100 |
| | 4MBr-5 | CRL 208 | 107 |
| | 12MBr6 | CRL 1576 | 137 |
| Mosquito | | | |
| larvae | Aedes aegypti | CCL 125 | 69 |
| | Aedes albopictus | CCL 126 | 70 |
| | Aedes albopictus, clone C6/36 | CRL 1660 | 149 |
| | TRA-171 | CRL 1591 | 139 |
| Moth | | | |
| ovary | Antheraea cells, adapted | CCL 80 | 45 |
| Mouse | | | |
| adrenal cortex | Y-1 | CCL 79 | 44 |
| ascites | E | CCL 77 | 43 |
| brain | BC₃H1 | CRL 1443 | 132 |
| carcinoma | KLN 205 | CRL 1453 | 132 |
| | SCC-PSA1 | CRL 1535 | 135 |
| connective tissue | L-M | CCL 1.2 | 2 |
| | L-M(TK⁻) | CCL 1.3 | 2 |
| | NCTC clone 929 | CCL 1 | 1 |
| | NCTC clone 2472 | CCL 11 | 9 |
| | NCTC clone 2555 | CCL 12 | 10 |
| | NCTC 2071 | CCL 1.1 | 1 |
| embryo | BALB/373 clone A31 | CCL 163 | 89 |
| | BALB/3T12-3 | CCL 164 | 91 |
| | C3H/MCA, clone 15 | CRL 1411 | 130 |
| | C3H/MCA, clone 16 | CRL 1412 | 131 |
| | C3H/10T1/2, clone 8 | CCL 226 | 116 |
| | K-BALB | CCL 163.3 | 90 |
| | M-MSV-BALB/3T3 | CCL 163.2 | 90 |
| | NCTC 4093 | CCL 63 | 35 |
| | NIH/3T3 | CRL 1658 | 146 |
| | SC-1 | CRL 1404 | 130 |
| | SV-T2 | CCL 163.1 | 89 |
| | 3T3-L1 | CCL 92.1 | 53 |
| | 3T3-Swiss albino | CCL 92 | 53 |
| | 3T6-Swiss-albino | CCL 96 | 55 |
| fibroblasts | BALB/B 0.75 BAE A.1R.1 HD A.8 | TIB 85 | 232 |
| | BALB/c AMuLV A.3R.1 | TIB 87 | 232 |
| | BALB/c AMuLV A.6R.1 | TIB 90 | 233 |
| | BALB/c CL.7 | TIB 80 | 232 |
| | BALB/c 10Cr MCA A.2R.1 | TIB 86 | 232 |
| | BALB/3T3 clone A31 | CCL 163 | 89 |
| | BLK CL4 | TIB 81 | 232 |
| | BLK SV HD.2 A.5R.1 A.3R.1 | TIB 88 | 232 |
| | C₃H/10T1/2 clone 8 | CCL 226 | 116 |
| | STO | CRL 1503 | 134 |
| | 3T3-L1 | CCL 92.1 | 53 |
| | 3T3-Swiss Albino | CCL 92 | 53 |
| keratinocytes | XB-2 | CL 177 | 95 |
| kidney | RAG | CCL 142 | 79 |
| | TCMK-1 | CCL 139 | 77 |
| liver | BNL CL.2 | TIB 73 | 231 |
| | BNL SV A.8 | TIB 74 | 232 |
| | BNL 1ME A.7R.1 | TIB 75 | 232 |
| | BNL 1NG A.2 | TIB 76 | 232 |
| | NCTC clone 1469 | CCL 9.1 | 8 |
| | NMuLi | CRL 1638 | 144 |
| lung | LA-4 | CCL 196 | 101 |
| | LL/2 | CRL 1642 | 144 |
| | MLg | CCL 206 | 106 |
| mammary tissue | CL-S1 | CRL 1615 | 142 |
| | C127I | CRL 1616 | 142 |
| | NMT 060562 | CCL 51 | 29 |
| | Mm5MT | CRL 1637 | 144 |

| Species/Tissue | Name | ATCC No. | Page No. |
|---|---|---|---|
| | MMuMG | CRL 1636 | 144 |
| mastocytoma | P815 | TIB 64 | 230 |
| melanoma | Clone-M-3 | CCL 53.1 | 29 |
| muscle | BC$_3$H1 | CRL 1443 | 132 |
| | BLO-11 | CCL 198 | 102 |
| | G-7 | CRL 1447 | 132 |
| | G-8 | CRL 1456 | 132 |
| | NOR 10 | CCL 197 | 102 |
| myeloblast | M1 | TIB 192 | 243 |
| neoroblastoma | NB41A3 | CCL 147 | 81 |
| | Neuro-2a | CCL 131 | 73 |
| pituitary | AoT-20 | CCL 89 | 51 |
| rectum | CMT-93 | CCL 223 | 115 |
| spleen | BCL$_1$ clone 5B1b | TIB 197 | 243 |
| sarcoma | CCRF S-180 II | CCL 8 | 7 |
| | HSDM$_1$C$_1$ | CCL 148 | 82 |
| | MB III | CCL 32 | 18 |
| | Sarcoma 180 | TIB 66 | 231 |
| testis | I-10 | CCL 83 | 47 |
| | NULLI-SCC1 | CRL 1566 | 137 |
| Pig | | | |
| kidney | ESK-4 | CL 184 | 96 |
| | LLC-PK$_{1A}$ | CL 101.1 | 58 |
| | LLC-PK$_1$ | CRL 1392 | 130 |
| | PK(15) | CCL 33 | 19 |
| | | | 250 |
| Potoroo | | | |
| kidney | PtK1 | CCL 35 | 21 |
| | PtK2 | CCL 56 | 31 |
| Rabbit | | | 251 |
| cornea | SIRC | CCL 60 | 33 |
| kidney | LLC-RK$_1$ | CCL 106 | 60 |
| | RK$_{13}$ | CCL 37 | 21 |
| lung | R 9ab | CCL 193 | 100 |
| skin | RAB-9 | CRL 1414 | 131 |
| | Sf 1 Ep | CCL 68 | 38 |
| Racoon | | | |
| uterus | PL 1 Ut | CCL 74 | 41 |
| Rat | | | |
| bladder | NBT-II | CRL 1655 | 146 |
| carcinoma | LLC-WRC 256 | CCL 38 | 21 |
| glia | C$_6$ | CCL 107 | 60 |
| heart | H9c2(2-1) | CRL 1446 | 132 |
| intestine | IA-XsSBR | CRL 1677 | 148 |
| lung | IEC-6 | CRL 1592 | 139 |
| | IEC-18 | CRL 1589 | 139 |
| kidney | KNRK | CRL 1569 | 137 |
| | NRK-49F | CRL 1570 | 137 |
| | NRK-52E | CRL 1571 | 137 |
| liver | BRL 3A | CRL 1442 | 132 |
| | Clone 9 | CRL 1439 | 131 |
| | H4TG | CRL 1576 | 137 |
| | H-4-II-E | CRL 1548 | 136 |
| | H4II-E-C3 | CRL 1600 | 140 |
| | McA-RH7777 | CRL 1601 | 140 |
| | McA-RH8994 | CRL 1602 | 140 |
| | MH$_1$C$_1$ | CCL 144 | 79 |
| | N1-SI | CRL 1604 | 141 |
| | N1-SI Fudr | CRL 1603 | 141 |
| lung | L2 | CCL 149 | 82 |
| | RFL-6 | CCL 192 | 99 |
| muscle | A7r5 | CRL 1444 | 132 |
| | A10 | CRL 1476 | 133 |
| | H9c2(2-1) | CRL 1446 | 132 |
| | L6 | CRL 1458 | 132 |
| pancreas | ARIP | CRL 1674 | 148 |
| | AR42J | CRL 1492 | 134 |
| pituitary | GH$_1$ | CCL 82 | 46 |
| | GH$_3$ | CCL 82.1 | 47 |
| pleura | 4/4R.M.-4 | CCL 216 | 110 |
| sarcoma | Jensen Sarcoma | CCL 45 | 25 |
| | RR 1022 | CCL 47 | 27 |
| | XC | CCL 165 | 92 |
| skin | FR | CRL 1213 | 130 |
| testis | LC-540 | CCL 43 | 24 |
| | R2C | CCL 97 | 56 |
| thyroid | FRTL | CRL 1468 | 133 |
| | 6-23 | CRL 1607 | 141 |
| Salmon | | | |
| embryo | CHSE-214 | CRL 1681 | 148 |
| Sheep | | | |
| brain | SCP | CRL 1700 | 149 |
| kidney | MDOK | CRL 1633 | 144 |
| Snail | | | |
| embryo | Bge | CRL 1494 | 134 |
| Toad | | | |
| kidney | A6 | CCL 102 | 58 |
| Trout | | | |
| gonad | RTG-2 | CCL 55 | 31 |
| Turtle | | | |
| heart | TH-1, subline B1 | CCL 50 | 28 |
| Viper | | | |
| heart | VH2 | CCL 140 | 78 |
| spleen | VSW | CCL 129 | 71 |

The culturing process of this invention is particularly advantageously applied to 293 cells derived from human fetal kidney cells, BHK cells (such as BHK-21 strain) derived from hamster, CHO cells (such as CHO-K1 strain) derived from hamster, COS cells (such as COS-1 strain and COS-7 strain) derived from monkey, rat HepI cells, rat HeP II cells, human lung cells (such as WI-38 strain), human lung cancer cells (such as HepG2 strain), mouse liver cells (such as BNLCL 2 strain), and DUKX cells. Of these, cells 293, derived from human fetal kidney cells, BHK cells, CHO cells, and transformants thereof are most suitable for the process of this invention.

Preparation of the transformants is carried out by a general method of transfecting an expression vector containing DNA having a base sequence encoding the amino acid sequence of the desired protein into host animal cells.

Examples of the expression vector which can be transfected into the adherent animal cells include expression vectors obtained by inserting DNAs encoding useful biologically active substances exemplified below into various vectors, for example viral vectors such as BLPV, AMIV and vacccinia virus) or plasmid vectors using promotors such as SV-40 early promoter, adenovirus MLP and LRSV promoter optionally together with a selection marker.

Examples of the useful biologically active substance which are encoded by DNAs to be inserted in the expression vectors are given below.

Hormones

Erythropoetin (EPO), growth hormone, insulin, beta-endorphin, calcitonin, somatostatin, growth hormone releasing factor (GRF), caerulein, cholecystokinin, corticotropin-releasing factor, alpha-neoendorphin, pituitary gonadotropine, glucagon, LH-PH, sodium diuretic peptide, oxytocin, parathyroid hormone, secretin, THR, vasopressin, proinsulin, luteinizing hormone, enkephalin, lipocortin, somatomedin, renin, angiotensin I, angiogenic factor, thiol protease inhibitor (TPI), $\alpha_1$-antitrypsin (AAT), collagenase inhibitor, glutathione, urogastron, and hirudine.

Cytokinins

Interferon (IFN), tumor necrosis factor (TNF), interleukin 1 (IL-1), interleukin 2 (IL-2), interleukin 3 (IL-3), interleukin 4 (IL-4), B cell differentiation factor (BCDF), T cell replacing factor (TRF) 2, NKCF, leukoregulin, macrophage activating factor (MCF) and leumorphin.

Coagulation fibrolytic proteins

Protein C (PC), activated protein C (APC), tissue plasminogen activator (TPA), thrombomodulin, urokinase (UK), prourokinase (pro-UK), streptokinase, blood coagulation factor VIII, blood coaglation factor IX, blood coagulation factor XIII, and tissue factor protein S.

Enzymes

Chymosin, elastase, superoxide dismutase, A-amylase, T-4 lysozyme, alkaline phosphatase, penicillinase, T-4 ligase, beta-lactamase, betaglucanase, beta-glucosidase, staphylokinase, lipase, penicillin G acylase, gutoamylase, pullulanase, cathechol-2,3-oygenase, prochymosin, metallothionein, oxyreductase and DNA ligase.

Vaccines

HBsAg, KEB virus antigenic protein, KATLV antigenic peptide, poliovirus antigenic protein, A-type heptatitis virus antigenic protein, HSV antigenic protein, FMDV antigenic protein, M protein of streptococcus, and diphtehric toxin antigenic proesin.

Blood constituents

Immunoglobulin, serum albumin, apolipoprotein E and apolipoprotein A-1.

Growth factor

Colony stimulation factor (CSF), epidermal growth factor (EGF), transforming growth factor (TGF), nerve growth factor (NGF), insulin-like growth factor, and macrophage proliferation factor.

Other Useful Biologically Active Substances

Protein A, beta-actin, and soybean storage protein (glycinin).

Especially preferably, the adherent animal cells are those which secrete protein C (PC) or activated protein C (APC) transfected by the above method.

The culturing method used in this invention is a method by which cells are cultured in suspension over a long period of time under controlled culture conditions while continuously or intermittently withdrawing from the culture vessel part of the spent medium with the cells contained therein or separated therefrom, and feeding a fresh medium in an amount corresponding to the amount of the medium withdrawn.

Simply stated, the culturing method of the invention may be said to be a perfusion-suspension culture method. One important point in the perfusion suspension culture is that living cells are efficiently separated from the culture broth, the spent medium is taken out of the culture vessel, and the cell living environment in the culture vessel is maintained under optimum conditions. The spent medium taken out from the culture vessel can be reused as a fresh medium by recovering useful substances contained in it or separating and removing growth inhibiting substances by means of a separating method by a membrane or a separation method by adsorption for cultivation, and adjusting the calcium ion to a predetermined level.

What is most important in the culture method of this invention is to maintain the calcium ion ($Ca^{++}$) concentration in the medium under the culturing conditions at 0.002 mM to 0.3 mM. The unit "mM" denotes the amount in millimoles of a calcium ion present in the aqueous medium (water) per liter. The calcium ion ($Ca^{++}$) means calcium metal based on a calcium compound present in a dissolved state in the medium.

The calcium ion concentration in the medium is preferably 0.02 mM to 0.25 mM, most preferably 0.05 mM to 0.20 mM. When cultured in a medium having a calcium ion concentration of more than 0.3 mM, the adherent animal cells adhere together and aggregate into many large clumps as the cultivation is continued. As the cultivation is further continued, they grow larger gradually, and the cells in the interior of the clumps die away. Furthermore, when clumps of a size above a certain limit form, the amount of a useful biologically active substance secreted per cell tends to decrease undesirably.

On the other hand, if the calcium ion concentration falls below the above-specified range, the cells no longer grow and in many cases die away. Even if the cells are growing, the amount of the useful biologically active substance secreted by the cells abruptly decreases, and the purpose of culture cannot be achieved.

According to this invention, by maintaining the calcium ion concentration in the medium under the culture conditions, the cells can be cultured for a long period of time as relatively small particles even if the cell density is as high as at least $3 \times 10^6$ cells/ml, preferably at least $5 \times 10^6$ cells/ml Under preferred conditions, suspension cultivation at a high density of $7 \times 10^6$ to $3 \times 10^7$ cells/ml can be performed.

In a preferred embodiment of this invention, most of the cells in the culture vessel, preferably at least 90% thereof, especially preferably at least 95% thereof, are maintained in suspension while forming relatively small particles each containing 1.1 to 50 cells on an average, preferably 1.5 to 30 cells on an average. This can be achieved by culturing the cells in a medium having the low calcium concentration specified above and the culture system is maintained in a good suspended state by agitation and/or aeration, and efficiently supplying a fresh medium and discharging the spent medium.

The simplest method of maintaining the calcium ion concentration in the medium under cultivation conditions is to control the calcium ion concentration of a fresh medium to be fed to the culture vessel to the aforesaid range. Specifically, it is simple to use a serum-free medium having a low calcium ion concentration as the fresh medium.

The serum-free medium used in this invention will now be described.

The cultivation in accordance with this invention is carried out substantially by using a serum-free medium which does not substantially contain proteins derived from a biological source such as serum. Any basal media heretofore used for cultivation in the presence of serum may be utilized as the serum-free medium. Examples include RPMI-1640 medium, Eagle's basal medium (BME), minimum essential medium (MEM), Isocove's medium, HAM F12 medium, L-15 medium, Williams' medium, Waymouth's medium and Dulbecco's modified Eagle's medium (DME). Most of these basal media are usually sold with a calcium ion concentration of 0.3 to 1.8 mM, especially 0.5 mM to 1.5 mM, and as they are, are unsuitable for use in the low calcium ion cultivation in accordance with this invention. Accordingly, it is necessary to prepare such basal media having a calcium concentration adjusted to a low concentration, for example 0.0026 mM, and optionally add a calcium ion to adjust the total calcium ion concentration to the level preferred in this invention. It is also possible to remove part of the calcium ion from one or a mixture of commercial basal media having a relatively high calcium ion concentration and to use the resulting media as a medium with a low calcium ion concentration.

The compositions of the above basal madia intrinsically require the addition of at least 10% of serum. In order to use them for serum-free cultivation in accordance with this invention, it is necessary to add various nutrients or growth factors or proliferation factors in place of the serum.

As required, up to 2% by volume of serum may be added to a serum-free medium adjusted to low calcium ion concentration so long as the calcium ion concentration is confined with the range specified in this invention. For from the viewpoint of reducing cell clumping, the cultivation at a low calcium ion concentration produces sufficient effect, but from the standpoint of proliferating and maintaining the cells, the addition of some amount of serum is preferred for some types of cells. The serum may be, for example, fetal calf serum (FCS), new-born calf serum (NBCS), calf serum (CS), or horse serum (HS).

In the case of adding such serum, the calcium ion concentration should be adjusted by considering the fact that usually the serum contains some amount of a calcium ion.

Instead of utilizing the commercial serum-free media, a culture media having a low calcium ion concentration specified in this invention may be prepared by adding components usually used for cell culture, such as inorganic salts, vitamins, coenzymes, glucose, amino acids and antibiotics and further a calcium salt such as calcium chloride or calcium nitrate or both to an aqueous medium composed substantially of water, and as required adding less than 3% by volume of serum.

Generally, cultivation of cells in suspension is started by sowing the cells at a relatively low density, for example about $5 \times 10^4$ to $1 \times 10^6$ cells/ml. At a density of up to about $3 \times 10^6$ cells/ml, the cells may be cultured by an ordinary known method, namely in a medium having a calcium ion concentration of at least 0.3 mM (serum-containing or serum-free medium), or in a low calcium ion medium in accordance with this invention. In the present invention when the cell density exceeds $3 \times 10^6$ cells/ml and the cells are in suspension, the low calcium ion medium described in this invention is used.

In the culturing process of this invention, the oxygen concentration of the culture medium is maintained constant by supplying oxygen, for example by directly supplying oxygen or an oxygen-containing gas to the suspension. As another means of supplying oxygen, an oxygen carrier, for example, may be used. The oxygen carrier is a liquid compound substantially immiscible with water and capable of dissolving oxygen. Examples are various fluorocarbons used as a material for artificial blood. When such fluorocarbons are used as means of dissolving oxygen, a fluorocarbon having dissolved oxygen therein may be added from above in the form of liquid droplets or a thin film. It is also possible to fix an oxygen-permeable Teflon or silicon tube to the inside of the culture vessel.

According to the process of this invention, adherent animal cells can be cultured in suspension continuously over a long period of time at a high cell density without the need to use an expensive microcarrier. Moreover, since this process uses a serum-free medium, it is inexpensive, and the useful biologically active substance can be easily separated from the recovered medium and purified.

In addition, since the suspension culture can be performed at a high cell density for a long period of time, the volume efficiency of the culture vessel is high and the useful biologically active substance can be produced in great quantities even in a relatively small culture vessel.

Another great advantage of this invention is that since in suspension, the cells mostly form small clumped particles each consisting of several to several tens of cells, the spent medium can be very smoothly taken out from the culture vessel. In a continuous operation of suspension culture of non-adherent cells, it is extremely difficult to take out the spent medium while avoiding inclusion of cells therein. However, no such difficulty occurs in the suspension culture in accordance with this invention.

Thus, according to this invention, the spent medium containing a relatively high concentration of the useful biologically active substance secreted by the cells can be withdrawn from the culture vessel continuously and smoothly. The process of this invention is very suitable for the industrial production of useful substances.

BRIEF DESCRIPTION OF THE DRAWING

The accompanying drawing is a schematic view of the culture vessel used in the following Examples of the invention.

The following Examples illustrate the present invention.

EXAMPLE 1

1) Culture Device

The culture system shown in the accompanying drawing was used. In this culture system, a settling zone partitioned by a wall inwardly of an outside wall is provided, and a discharge port for the culture medium is provided at the top. The net capacity of the culture system is about 180 ml.

2) Culture Medium

The basal medium used was prepared by mixing RPMI 1640 medium, HAM F12 medium and Dulbecco modified Eagle's medium in a ratio of 2:1:1, adding glucose, amino acids, etc. (the resulting mixture is referred to as eRDF), and decreasing the calcium ion concentration of the mixture to 0.1 mM from usual 0.74 mM. Insulin, transferrin, ethanolamine and sodium selenite (to be referred to as ITES) were added as proliferation factor in a concentration of 9 $\mu$g/ml, 10 $\mu$g/ml, 10 $\mu$M, and 20 nm, respectively. 3) Method and Result of Culturing The culture medium was fed to a net culture volume of about 180 ml into the culture vessel which had previously been autoclaved. Strain 293 originated from fetal kidney cells and obtained from ATCC were seeded in the culture vessel at a density of $0.8 \times 10^6$ cells/ml.

Oxygen gas was fed to the culture vessel through blowing nozzle (B) with automatic control so that the concentration of dissolved oxygen became 3 ppm. The culture medium in the culture vessel was maintained at 37° C. A marine-type agitating impeller was set in the culture vessel and was rotated at a speed of 40 rpm.

The culturing was carried out batchwise for one day after the seeding, and thereafter, perfusion was started.

Pump P was operated, and the culture medium separated from the cells in the culture vessel was withdrawn from line (D), and a fresh medium in the same amount as that of the withdrawn medium was continuously fed into the culture vessel from line (A). With time, the cell density increased, and on the 6th day, reached $15 \times 10^6$ cells/ml. Thereafter, the proliferation of the cells showed a steady state. The culturing was continued for 30 days. The results are shown in Table 1.

TABLE 1

Cell: Strain 293
Medium: ITES-eRDF (calcium ion 0.15 mM)

| Culturing time (days) | Medium replacement (ml/day) | Living cell density ($\times 10^6$ cells/ml) |
| --- | --- | --- |
| 0 | 0 | 0.8 |
| 2 | 140 | 2.0 |
| 4 | 140 | 4.8 |
| 6 | 140 | 15 |
| 8 | 280 | 22 |
| 10 | 280 | 23 |
| 12 | 280 | 18 |
| 14 | 280 | 18 |
| 16 | 280 | 20 |
| 18 | 280 | 17 |
| 20 | 280 | 15 |
| 22 | 280 | 18 |
| 24 | 280 | 21 |
| 26 | 280 | 23 |
| 28 | 280 | 23 |
| 30 | 280 | 20 |

The average degree of aggregation in a steady state was 5 cells per particle.

COMPARATIVE EXAMPLE 1

Example 1 was repeated except that a culture medium (ITES-eRDF) having a usual calcium concentration (0.74 mM) was used instead of the culture medium used in Example 1. The results are shown in Table 2.

TABLE 2

Cell: Strain 293
Medium: ITES-eRDF (calcium ion 0.74 mM)

| Culturing time (days) | Medium replacement (ml/day) | Living cell density ($\times 10^6$ cells/ml) |
| --- | --- | --- |
| 0 | 0 | 0.8 |
| 2 | 140 | 1.3 |
| 4 | 280 | 5.0 |
| 6 | 280 | 13 |
| 8 | 280 | 17 |
| 10 | 280 | 32 |
| 12 | 280 | 24 |
| 14 | 280 | 18 |
| 16 | 280 | 18 |
| 18 | 280 | 10 |
| 20 | 280 | 8 |
| 22 | 280 | 5 |
| 24 | 280 | 3 |
| 26 | 280 | 1.3 |
| 28 | 280 | 0.5 |
| 30 | 280 | 0.2 |

The average degree of aggregation in a steady state was $7 \times 10^3$ cells per particle.

EXAMPLE 2

1) Culture Device

The culture system shown in the accompanying drawing was used. In this culture system, a settling zone partitioned by a wall inwardly of an outside wall is provided, and a discharge port for the culture medium is provided at the top. The net capacity of the culture system is about 180 ml.

2) Culture Medium

The basal medium used was prepared by mixing RPMI 1640 medium, HAM F12 medium and Dulbecco modified Eagle's medium in a ratio of 2:1:1, adding glucose, amino acid, etc. (the resulting mixture is referred to as eRDF), and removing calcium salts (calcium chloride, calcium nitrate) other than calcium panthotenate (the resulting medium is referred to as low Ca eRDF). Insulin, transferrin, ethanolamine and sodium selenite IITES) was added as proliferation factors in a concentration of 9 μg/ml, 10 μg/ml, 10 μM and 20 nM, respectively.

3) Method and Result of Culturing

The culture medium was fed to a net culture volume of about 180 ml into the culture vessel- which had previously been autoclaved. Protein C-producing strain 293 #3, which had been obtained by introducing a DNA fragment encoding the amino acid sequence of human protein C in accordance with the method described in Japanese Laid-Open Patent Publication No. 111690/1987 into strain 293 originated from human fetal kidney cells procured from ATCC, was seeded in the culture medium.

Oxygen gas was fed into the culture vessel through blowing nozzle (B) with automatic control so that the concentration of dissolved oxygen became 3 ppm.

The culture medium in the vessel was maintained at 37° C. A marine-type agitation impeller was set in the culture vessel, and rotated at a speed of 40 rpm.

The culturing was carried out batchwise for one day after the seeding, and then perfusion was started. Pump P was operated, and the medium separated from the cells in the culture vessel was withdrawn from line (D), and a fresh medium in the same amount as that of the withdrawn medium was continuously fed from line (A).

The results and the number of medium replacements are shown in Table 3.

TABLE 3

Cells: 293 #3 strain
Medium: ITES + low Ca eRDF ($Ca^{++}$ was only 0.0026 mM from calcium panthotenate)

| Culturing time (day) | Medium replacement (ml/day) | Living cell density ($\times 10^6$ cells/ml) | PC (μg/ml) | (mg/day) |
| --- | --- | --- | --- | --- |
| 0 | 0 | 1.0 | — | — |
| 2 | 140 | 2.4 | 0.26 | 0.04 |
| 3 | 140 | 2.7 | 0.31 | 0.04 |
| 4 | 140 | 4.7 | 0.88 | 0.12 |
| 5 | 280 | 5.6 | 1.4 | 0.39 |
| 6 | 280 | 8.4 | 1.5 | 0.42 |
| 7 | 280 | 14 | 1.1 | 0.31 |

The average degree of aggregation in a steady state was 7 cells per particle.

COMPARATIVE EXAMPLE 2

Example 2 was repeated except that usual eRDF ($Ca^{++}$ concentration 0.74) was used instead of the eRDF used in Comparative Example 2.

The results are shown in Table 4.

TABLE 4

Cells: 283 #3 strain
Medium: ITES + eRDF (with a usual calcium ion concentration of 0.74 mM)

| Culturing time (day) | Medium replacement (ml/day) | Living cell density ($\times 10^6$ cells/ml) | PC (μg/ml) | (mg/day) |
| --- | --- | --- | --- | --- |
| 0 | 0 | 1.0 | — | — |

TABLE 4-continued

Cells: 283 #3 strain
Medium: ITES + eRDF (with a usual calcium ion concentration of 0.74 mM)

| Culturing time (day) | Medium replacement (ml/day) | Living cell density (× 10⁶ cells/ml) | PC (μg/ml) | PC (mg/day) |
|---|---|---|---|---|
| 1 | 140 | 0.9 | 0.82 | 0.11 |
| 3 | 140 | 3.6 | 2.2 | 0.31 |
| 5 | 280 | 4.0 | 2.2 | 0.62 |
| 7 | 280 | 4.7 | 2.2 | 0.62 |
| 11 | 280 | 5.8 | 1.9 | 0.53 |
| 13 | 280 | 4.6 | 1.1 | 0.31 |
| 15 | 280 | 4.0 | 0.66 | 0.18 |
| 18 | 280 | 3.7 | 0.56 | 0.16 |
| 20 | 280 | 3.7 | 0.22 | 0.06 |

The average degree of aggregation in a steady state was $2 \times 10^3$ cells per particle.

EXAMPLE 3

Example 2 was repeated except that 0.01 mM calcium chloride was further added to the culture medium.
The results are shown in Table 5.

TABLE 5

Cells: 393 #3 strain
Medium: 0.01 mM CaCl₂ + ITES + low Ca eRDF

| Culturing time (day) | Medium replacement (ml/day) | Living cell density (× 10⁶ cells/ml) | PC (μg/ml) | PC (mg/day) |
|---|---|---|---|---|
| 0 | 0 | 0.9 | — | — |
| 2 | 140 | 2.1 | 1.2 | 0.17 |
| 3 | 140 | 3.3 | 1.4 | 0.20 |
| 4 | 140 | 5.8 | 2.1 | 0.29 |
| 5 | 280 | 8.3 | 2.3 | 0.64 |
| 6 | 280 | 17 | 2.7 | 0.76 |
| 7 | 280 | 21 | 2.4 | 0.67 |

The average degree of aggregation in a steady state was 8 cells per particle.

EXAMPLE 4

Example 2 was repeated except that 0.04 mM calcium chloride was further added to the culture medium.
The results are shown in Table 6.

TABLE 6

Cells: 293 #3
Culture medium: 0.04 mM CaCl₂ + ITES + low Ca eRDF

| Culturing time (day) | Medium replacement (ml/day) | Living cell density (× 10⁶ cells/ml) | PC (μg/ml) | PC (mg/day) |
|---|---|---|---|---|
| 0 | 0 | 0.9 | — | — |
| 2 | 140 | 2.1 | 1.8 | 0.25 |
| 3 | 140 | 2.8 | 2.1 | 0.29 |
| 4 | 140 | 5.4 | 4.7 | 0.66 |
| 5 | 280 | 8.7 | 4.5 | 1.3 |
| 6 | 280 | 14 | 3.3 | 0.92 |
| 7 | 280 | 19 | 3.4 | 0.95 |

The average degree of aggregation in a steady state was 7 cells per particle.

EXAMPLE 5

Example 2 was repeated except that 0.1 mM calcium chloride was added to the culture medium.
The results are shown in Table 7.

TABLE 7

Cells: 293 #3
Medium: 0.1 mM CaCl₂ + ITES + low Ca eRDF

| Culturing time (day) | Medium replacement (ml/day) | Living cell density (× 10⁶ cells/ml) | PC (μg/ml) | PC (mg/day) |
|---|---|---|---|---|
| 0 | 0 | 0.9 | — | — |
| 2 | 140 | 1.5 | 1.0 | 0.14 |
| 3 | 140 | 2.1 | — | — |
| 4 | 140 | — | 1.6 | 0.22 |
| 6 | 280 | 8.0 | 3.6 | 1.0 |
| 7 | 280 | 12 | 5.8 | 1.6 |
| 9 | 420 | 14 | 4.1 | 1.7 |
| 10 | 420 | 12 | 4.2 | 1.8 |
| 12 | 420 | 11 | 3.9 | 1.6 |
| 14 | 420 | 14 | 4.0 | 1.7 |
| 17 | 420 | 18 | 3.2 | 1.3 |
| 20 | 420 | 19 | 3.0 | 1.3 |
| 22 | 420 | 15 | 3.1 | 1.3 |
| 23 | 420 | 14 | 4.1 | 1.7 |
| 27 | 420 | 12 | 2.7 | 1.1 |
| 29 | 420 | 13 | 2.2 | 0.92 |

The average degree of aggregation in a steady state was 6 cells per particle.

EXAMPLE 6

Example 2 was repeated except that protein C-producing strain BHK 229-10 obtained by introducing a DNA fragment encoding the amino acid sequence of human protein C into BHK strain procured from ATCC was used as the cells to be cultured; up to the 13th day, the culturing was carried out by using the medium used in Example 3; and that on the 14th day and onwards, the cultivation was carried out by using the medium used in Comparative Example 2.

The results are shown in Table 8.

TABLE 8

Cells: BHK 229-10
Medium:
(A) 0.01 mM CaCl₂ + ITES + low Ca eRDF
(B) ITES + eRDF (usual calcium ion concentration 0.74 mM)

| Culturing time (day) | Medium | Medium replacement (ml/day) | Living cell density (× 10⁶ cells/ml) | PC (μg/ml) | PC (mg/day) |
|---|---|---|---|---|---|
| 0 | A | 0 | 1.0 | — | — |
| 1 | A | 80 | 1.2 | — | — |
| 2 | A | 240 | 1.5 | — | — |
| 4 | A | 240 | 2.2 | 0.23 | 0.22 |
| 6 | A | 240 | 2.9 | 0.33 | 0.08 |
| 7 | A | 430 | 3.4 | 0.21 | 0.09 |
| 8 | A | 430 | 4.9 | 0.44 | 0.19 |
| 9 | A | 430 | 7.0 | — | — |
| 10 | A | 430 | 8.0 | 0.27 | 0.12 |
| 13 | A | 560 | 7.4 | 0.26 | 0.15 |
| 14 | B | 560 | about 7.0 | 2.1 | 1.2 |
| 15 | B | 560 | about 7.0 | 3.3 | 1.8 |
| 19 | B | 560 | about 7.0 | 2.9 | 1.6 |
| 21 | B | 560 | about 7.0 | 2.5 | 1.4 |
| 23 | B | 560 | about 7.0 | 2.2 | 1.2 |

The average degree of aggregation in a steady state was 40 cells per particle.

Table 8 shows that when BHK cells were cultivated in a low calcium medium for a certain period of time, and then in a medium having a usual calcium ion concentration, the cell clumps did not become large, and the cells could be cultured in suspension.

COMPARATIVE EXAMPLE 3

Example 6 was repeated except that the culture medium used in Comparative Example 1 was used throughout the cultivation period.

The results are shown in Table 9.

TABLE 9

Cells: BHK 229-10 strain
Medium: ITES + eRDF (usual calcium ion concentration 0.74 mM)

| Culturing time (day) | Medium replacement (ml/day) | Living cell density ($\times 10^6$ cells/ml) | PC ($\mu$g/ml) | PC (mg/day) |
| --- | --- | --- | --- | --- |
| 0 | 0 | 1.0 | — | — |
| 2 | 140 | 0.9 | 3.2 | 0.45 |
| 8 | 140 | 0.3 | 1.0 | 0.14 |
| 14 | 140 | 0.2 | 1.0 | 0.14 |
| 22 | 140 | 0.5 | 1.6 | 0.22 |
| 30 | 140 | 0.6 | 1.2 | 0.17 |

The average degree of aggregation in a steady state was $3 \times 10^4$ cells per particle.

EXAMPLE 7

Example 5 was repeated except that protein C-producing CHO Z4-I5 strain obtained by introducing a DNA fragment encoding the amino acid sequence of human protein C into CHO strain were used instead of the cells cultured in example 5.

The results are shown in Table 10.

TABLE 10

Cells: CHO Z4-I5 strain
Medium: 0.1 mM CaCl$_2$ + ITES + low Ca eRDF

| Culturing time (day) | Medium replacement (ml/day) | Living cell density ($\times 10^6$ cells/ml) | PC ($\mu$g/ml) | PC (mg/day) |
| --- | --- | --- | --- | --- |
| 0 | 0 | 0.5 | — | — |
| 3 | 140 | 1.5 | 5.2 | 0.73 |
| 4 | 140 | 2.1 | 5.5 | 0.77 |
| 6 | 140 | 2.7 | 6.0 | 0.84 |
| 7 | 280 | 5.0 | 4.9 | 1.4 |
| 10 | 430 | 7.0 | 4.9 | 2.1 |
| 12 | 560 | 9.9 | 6.2 | 3.5 |

The average degree of aggregation in a steady state was 30 cells per particle.

We claim:

1. A process for continuously culturing adherent animal cells selected from the group consisting of 293 strain derived from human fetal kidney cells and tranformants thereof, which cells are capable of secreting protein C in a serum-free medium, comprising:
   feeding fresh medium into a culture vessel, and withdrawing spent medium from the vessel,
   maintaining the said adherent animal cells in the serum-free medium in the said vessel in suspension,
   the said adherent animal cells being maintained in suspension at a density of at least $3 \times 10^6$ cells/ml,
   the concentration of calcium ion in the medium under the culturing conditions being maintained at 0.002 mM to 0.3 mM, and
   the protein C production level being at least 0.1 $\mu$g/$10^6$ cell/day for a period of about 30 days or longer.

2. The process of claim 1 in which the concentration of a calcium ion in the medium under the culturing conditions is maintained 0.002 mM to 0.25 mM.

3. The process of claim 1 or 2 in which most of the adherent animal cells in suspension are present as aggregated particles each containing 1.5 to 50 cells on an average.

4. The process of claim 1 or 2 in which most of the adherent animal cells in suspension are present as aggregated particles each containing 1.5 to 30 cells on an average.

5. The process of claim 1 in which the adherent animal cells in suspension are present at a density of at least $5 \times 10^6$ cells/ml.

6. The process of claim 1 in which the feeding of the fresh medium, and the withdrawal of the spent medium, into and from the culture vessel are carried out continuously or intermittently, and the liquid level in the culture vessel is maintained substantially constant.

7. The process of claim 1 in which the suspended state of the adherent animal cells in the culture vessel is maintained by agitation and/or aeration.

* * * * *